United States Patent
Hoye et al.

(10) Patent No.: US 11,672,551 B2
(45) Date of Patent: Jun. 13, 2023

(54) DUAL-LUMEN ULTRASONIC CATHETERS, SYSTEMS, AND METHODS

(71) Applicant: C.R. Bard, Inc., Franklin Lakes, NJ (US)

(72) Inventors: Jessica Lynn Roll Hoye, Phoenix, AZ (US); Amanda Young, Phoenix, AZ (US); William E. Parmentier, Gilbert, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 800 days.

(21) Appl. No.: 16/604,760

(22) PCT Filed: Apr. 28, 2017

(86) PCT No.: PCT/US2017/030266
§ 371 (c)(1),
(2) Date: Oct. 11, 2019

(87) PCT Pub. No.: WO2018/200004
PCT Pub. Date: Nov. 1, 2018

(65) Prior Publication Data
US 2021/0059697 A1    Mar. 4, 2021

(51) Int. Cl.
*A61B 17/22* (2006.01)
*A61M 25/00* (2006.01)
(Continued)

(52) U.S. Cl.
CPC ............. *A61B 17/22012* (2013.01); *A61M 25/0009* (2013.01); *A61M 25/0026* (2013.01);
(Continued)

(58) Field of Classification Search
CPC .......... A61B 17/2204; A61B 17/22012; A61B 2017/00526; A61B 2017/00973;
(Continued)

(56) References Cited

U.S. PATENT DOCUMENTS 5,024,234 A    6/1991  Leary et al.
5,554,163 A    9/1996  Shturman
(Continued)

FOREIGN PATENT DOCUMENTS

JP    2009504338 A    2/2009
JP    2011500286 A    1/2011
(Continued)

OTHER PUBLICATIONS

Office Action dated Apr. 9, 2021 from Japanese Application No. 2019-558375. (English Translation).
(Continued)

*Primary Examiner* — Kankindi Rwego
(74) *Attorney, Agent, or Firm* — Dinsmore & Shohl LLP

(57) ABSTRACT

Provided herein are dual-lumen catheters, systems, and methods thereof. In some embodiments, for example, a catheter assembly configured for modifying intravascular lesions is provided including a core wire, a dual-lumen extrusion including the core wire, and a manifold disposed around a portion of the dual-lumen extrusion. The core wire includes a proximal end configured to vibrationally couple to an ultrasound transducer. The dual-lumen extrusion includes a first lumen and a second lumen. The core wire is disposed within the first lumen, and the second lumen is configured to accommodate a guidewire. The manifold is disposed around at least a skived proximal-end portion of the dual-lumen extrusion, wherein the skived portion includes the second lumen without the first lumen. In some embodiments, the catheter assembly further includes the ultrasound transducer. In some embodiments, a system console includes the ultrasound transducer.

10 Claims, 5 Drawing Sheets

Figure 1:
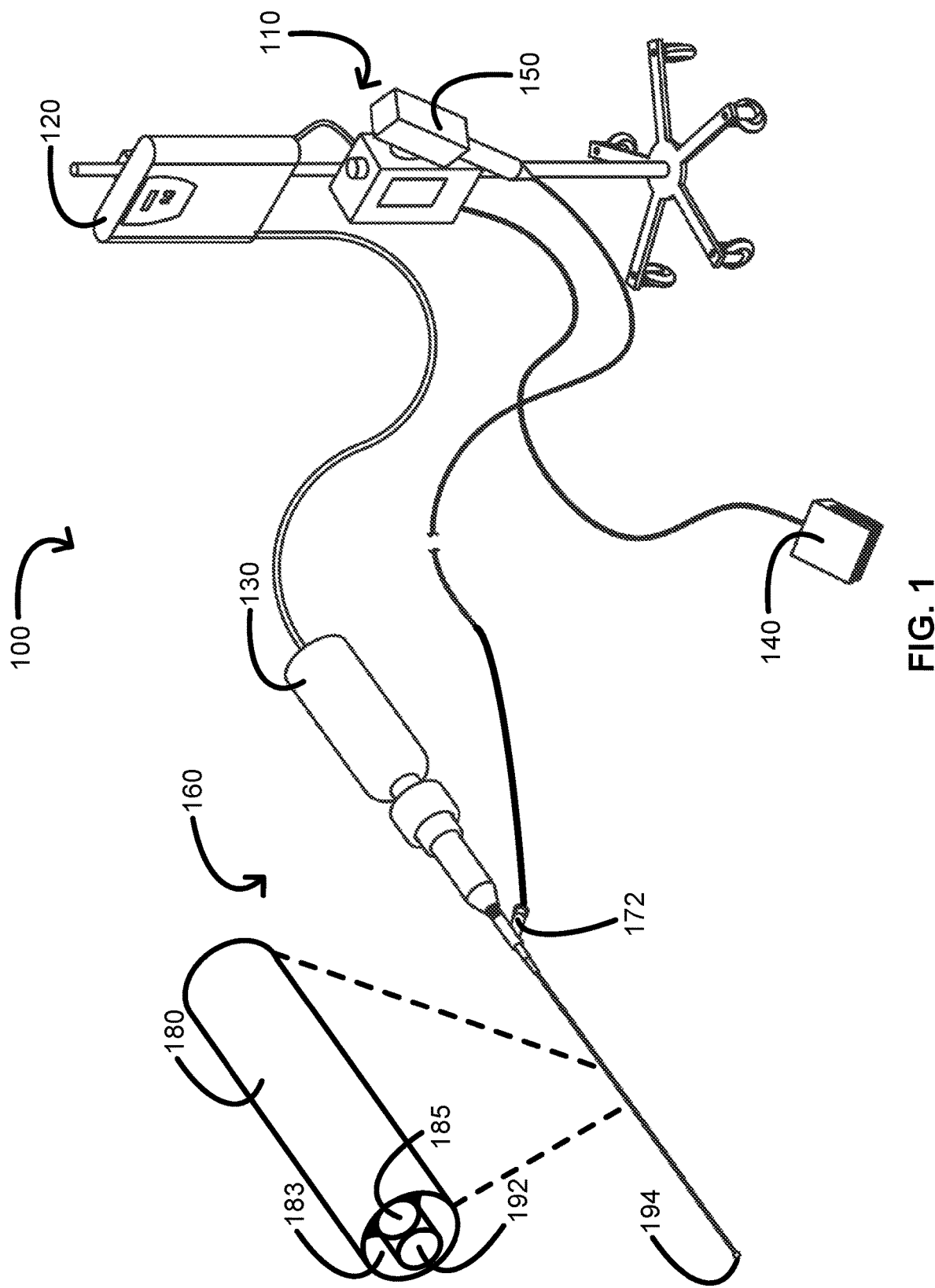

(51) Int. Cl.
  *A61M 25/09* (2006.01)
  *A61B 17/00* (2006.01)
(52) U.S. Cl.
  CPC .............. *A61M 25/09* (2013.01); *A61B 2017/00526* (2013.01); *A61B 2017/00973* (2013.01)
(58) Field of Classification Search
  CPC ..... A61B 2017/22011; A61M 25/0009; A61M 25/0026; A61M 25/0029; A61M 25/0169; A61M 2025/0004; A61M 2025/0034; A61M 2025/018; A61M 2025/0183
  USPC ................................................ 606/127, 128
  See application file for complete search history.

(56) References Cited

U.S. PATENT DOCUMENTS

| | | |
|---|---|---|
| 6,296,620 B1 | 10/2001 | Gesswein |
| 6,461,383 B1 | 10/2002 | Gesswein et al. |
| 8,206,370 B2 | 6/2012 | von Oepen et al. |
| 2005/0070878 A1* | 3/2005 | Triplett ............. A61M 25/0097 604/523 |
| 2006/0122507 A1 | 6/2006 | Rule et al. |
| 2007/0078437 A1 | 4/2007 | Borden et al. |
| 2008/0319376 A1 | 12/2008 | Wilcox et al. |
| 2010/0036256 A1* | 2/2010 | Boukhny ............ A61F 9/00745 600/459 |
| 2011/0046522 A1 | 2/2011 | Chan et al. |
| 2016/0302762 A1 | 10/2016 | Stigall et al. |
| 2016/0361528 A1 | 12/2016 | Kanz et al. |
| 2017/0080181 A1 | 3/2017 | Shiono et al. |

FOREIGN PATENT DOCUMENTS

| | | |
|---|---|---|
| WO | 20070022278 W | 2/2007 |
| WO | 20090055651 W | 4/2009 |
| WO | 2016081026 A1 | 5/2016 |

OTHER PUBLICATIONS

Office Action dated Jan. 12, 2023, pertaining to Japanese Patent Application 2022-35190.

* cited by examiner

DUAL-LUMEN ULTRASONIC CATHETERS, SYSTEMS, AND METHODS

CROSS-REFERENCE TO RELATED APPLICATIONS

This application is a U.S. national phase of International Application No. PCT/US2017/030266, filed Apr. 28, 2017, which is incorporated herein by reference in its entirety.

BACKGROUND

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen. Surgical procedures for atherosclerosis such as angioplasty or atherectomy can be used to restore patency and blood flow lost to the one or more intravascular lesions.

An atherosclerotic surgical procedure can involve advancing one or more endoluminal devices to an intravascular lesion to modify the intravascular lesion. For example, angioplasty or atherectomy can involve advancing an over-the-wire ("OTW") endoluminal device over a guidewire in a guidewire lumen of the endoluminal device to an intravascular lesion for modification thereof. However, advancing the OTW endoluminal device to the intravascular lesion can lead to surgical issues from device complications, especially in OTW endoluminal devices having poorly designed or manufactured tube-within-tube designs. For example, a separately extruded, guidewire lumen-containing guidewire tube insufficiently tacked to an inner wall of a sheath of an OTW endoluminal device can lead to device complications such as twisting of portions of the guidewire tube able to move independently from the sheath. Provided herein in some embodiments are dual-lumen catheters, systems, and methods that address the foregoing.

SUMMARY

Provided herein is a catheter assembly configured for modifying intravascular lesions including, in some embodiments, a core wire, a dual-lumen extrusion including the core wire, and a manifold disposed around a portion of the dual-lumen extrusion. The core wire includes a proximal end configured to vibrationally couple to an ultrasound transducer. The dual-lumen extrusion includes a first lumen and a second lumen. The core wire is disposed within the first lumen, and the second lumen is configured to accommodate a guidewire. The manifold is disposed around at least a skived proximal-end portion of the dual-lumen extrusion, wherein the skived portion includes the second lumen without the first lumen.

In such embodiments, the second lumen is disposed within the first lumen in the dual-lumen extrusion.

In such embodiments, the skived portion of the dual-lumen extrusion is less than or equal to about 35 mm long.

In such embodiments, the skived portion of the dual-lumen extrusion is disposed in a support tube. The manifold is disposed around the support tube, the skived portion, and an adjoining portion of the dual-lumen extrusion including the first lumen and the second lumen.

In such embodiments, the catheter assembly further includes a tip member seated in a distal end of the dual-lumen extrusion. The second lumen of the dual-lumen extrusion extends through the tip member enabling a guidewire to pass through the tip member.

In such embodiments, a distal end of the dual-lumen extrusion includes a flared portion of the dual-lumen extrusion. A sized-matched piece of guidewire tubing is disposed in the flared portion extending the second lumen of the dual-lumen extrusion through the tip member.

In such embodiments, the catheter assembly further includes an ultrasound transducer at the proximal end of the core wire.

Also provided herein is a system configured for modifying intravascular lesions, including, in some embodiments a catheter assembly and an ultrasonic energy-producing mechanism. The catheter assembly includes a core wire, a dual-lumen extrusion including the core wire, and a manifold disposed around a portion of the dual-lumen extrusion. The dual-lumen extrusion includes a first lumen and a second lumen. The core wire is disposed within the first lumen, and the second lumen is configured to accommodate a guidewire. The manifold is disposed around at least a skived proximal-end portion of the dual-lumen extrusion, wherein the skived portion includes the second lumen without the first lumen. The ultrasonic energy-producing mechanism includes an ultrasound generator and an ultrasound transducer. The core wire includes a proximal end configured to vibrationally couple to the ultrasound transducer.

In such embodiments, the second lumen is disposed within the first lumen in the dual-lumen extrusion. The second lumen shares at least a portion of lumen wall with the first lumen.

In such embodiments, the skived portion of the dual-lumen extrusion is less than or equal to about 35 mm long.

In such embodiments, the skived portion of the dual-lumen extrusion is disposed in a support tube. The manifold is disposed around the support tube, the skived portion, and an adjoining portion of the dual-lumen extrusion including the first lumen and the second lumen.

In such embodiments, the system further includes a tip member seated in a distal end of the dual-lumen extrusion. The second lumen of the dual-lumen extrusion extends through the tip member enabling a guidewire to pass through the tip member.

In such embodiments, a distal end of the dual-lumen extrusion includes a flared portion of the dual-lumen extrusion. A sized-matched piece of guidewire tubing is disposed in the flared portion extending the second lumen of the dual-lumen extrusion through the tip member.

In such embodiments, the system further includes a console including a foot switch and the ultrasonic energy-producing mechanism including the ultrasound generator and the ultrasound transducer. The foot switch is configured to activate and deactivate the ultrasonic energy-producing mechanism.

In such embodiments, the system further includes a console including a foot switch and the ultrasound generator of the ultrasonic energy-producing mechanism. The catheter assembly further includes the ultrasound transducer of the ultrasonic energy-producing mechanism. The foot switch is configured to activate and deactivate the ultrasonic energy-producing mechanism.

Also provided herein is catheter assembly configured for modifying intravascular lesions including, in some embodiments, a core wire, a dual-tube extrusion including the core wire, and a manifold disposed around a portion of the dual-tube extrusion. The core wire includes a proximal end configured to vibrationally couple to an ultrasound transducer. The dual-tube extrusion includes a first tube with a first lumen and a second tube with a second lumen. The core wire is disposed within the first lumen, and the second lumen is configured to accommodate a guidewire. The manifold is disposed around at least a skived proximal-end portion of the dual-tube extrusion, wherein the skived portion includes the second tube without the first tube.

In such embodiments, the second tube is disposed within the first tube of the dual-tube extrusion. The second tube shares at least a portion of a tube wall with the first tube when disposed therein.

In such embodiments, the second tube of the skived portion of the dual-tube extrusion is disposed in a support tube. The manifold is disposed around the support tube, the skived portion, and an adjoining portion of the dual-tube extrusion including the first tube and the second tube.

In such embodiments, the system further includes a tip member seated in a distal end of the dual-tube extrusion. The second lumen of the dual-tube extrusion extends through the tip member enabling a guidewire to pass through the tip member.

In such embodiments, a distal end of the dual-tube extrusion includes a flared portion of the second tube. A size-matched piece of guidewire tubing is disposed in the flared portion of the second tube extending the second lumen of the dual-tube extrusion through the tip member.

Also provided herein is system configured for modifying intravascular lesions including, in some embodiments, a catheter assembly and an ultrasonic energy-producing mechanism. The catheter assembly includes a core wire, a dual-tube extrusion including the core wire, and a manifold disposed around a portion of the dual-tube extrusion. The dual-tube extrusion includes a first tube with a first lumen and a second tube with a second lumen. The core wire is disposed within the first lumen, and the second lumen is configured to accommodate a guidewire. The manifold is disposed around at least a skived proximal-end portion of the dual-tube extrusion, wherein the skived portion includes the second tube without the first tube. The ultrasonic energy-producing mechanism includes an ultrasound generator and an ultrasound transducer. The core wire includes a proximal end configured to vibrationally couple to the ultrasound transducer.

In such embodiments, the second tube is disposed within the first tube of the dual-tube extrusion. The second tube shares at least a portion of a tube wall with the first tube when disposed therein.

In such embodiments, the second tube of the skived portion of the dual-tube extrusion is disposed in a support tube. The manifold is disposed around the support tube, the skived portion, and an adjoining portion of the dual-tube extrusion including the first tube and the second tube.

In such embodiments, the system further includes a tip member seated in a distal end of the dual-tube extrusion. The second lumen of the dual-tube extrusion extends through the tip member enabling a guidewire to pass through the tip member.

In such embodiments, a distal end of the dual-tube extrusion includes a flared portion of the second tube. A size-matched piece of guidewire tubing is disposed in the flared portion of the second tube extending the second lumen of the dual-tube extrusion through the tip member.

In such embodiments, the system further includes a console including a foot switch and the ultrasonic energy-producing mechanism including the ultrasound generator and the ultrasound transducer. The foot switch is configured to activate and deactivate the ultrasonic energy-producing mechanism.

In such embodiments, the system further includes a console including a foot switch and the ultrasound generator of the ultrasonic energy-producing mechanism. The catheter assembly further includes the ultrasound transducer of the ultrasonic energy-producing mechanism. The foot switch is configured to activate and deactivate the ultrasonic energy-producing mechanism.

Also provided herein is a method for manufacturing a catheter assembly configured for modifying intravascular lesions including, in some embodiments, extruding a dual-tube extrusion, skiving off a portion of the dual-tube extrusion, flaring another portion of the dual-tube extrusion, disposing the dual-tube extrusion in a manifold, and seating a tip member in the dual-tube extrusion. Extruding the dual-tube extrusion includes extruding a first tube with a first lumen and a second tube with a second lumen. The first lumen is configured for disposing a core wire therein. The second lumen is configured to accommodate a guidewire. Skiving off the portion of the dual-tube extrusion includes skiving off the first tube in a proximal-end portion of the dual-tube extrusion to provide a skived portion of the dual-tube extrusion including the second tube without the first tube. Flaring the other portion of the dual-tube extrusion includes flaring the second tube in a distal-end portion of the dual-tube extrusion to provide a flared portion of the second tube. Disposing the dual-tube extrusion in the manifold includes disposing at least the skived portion of the dual-tube extrusion in the manifold. Seating the tip member in the dual-tube extrusion includes seating a lesion-modifying tip member in a distal end of the dual-tube extrusion.

In such embodiments, the second tube is disposed within the first tube in the dual-tube extrusion. The second tube and the first tube share a wall.

In such embodiments, the method further includes disposing the second tube of the skived portion of the dual-tube extrusion in a support tube. Subsequently, the support tube including the skived portion is disposed in the manifold with an adjoining portion of the dual-tube extrusion including the first tube and the second tube.

In such embodiments, the method further includes attaching a guidewire hub to the support tube.

In such embodiments, the method further includes disposing a size-matched piece of guidewire tubing in the flared portion of the second tube. Subsequently, the tip member is seated in the distal end of the dual-tube extrusion.

In such embodiments, the method further includes disposing a core wire in the first lumen.

These and other features of the concepts provided herein may be better understood with reference to the drawings, description, and appended claims.

DRAWINGS

FIG. 1 provides a schematic illustrating a system in accordance with some embodiments.

Figure 2:
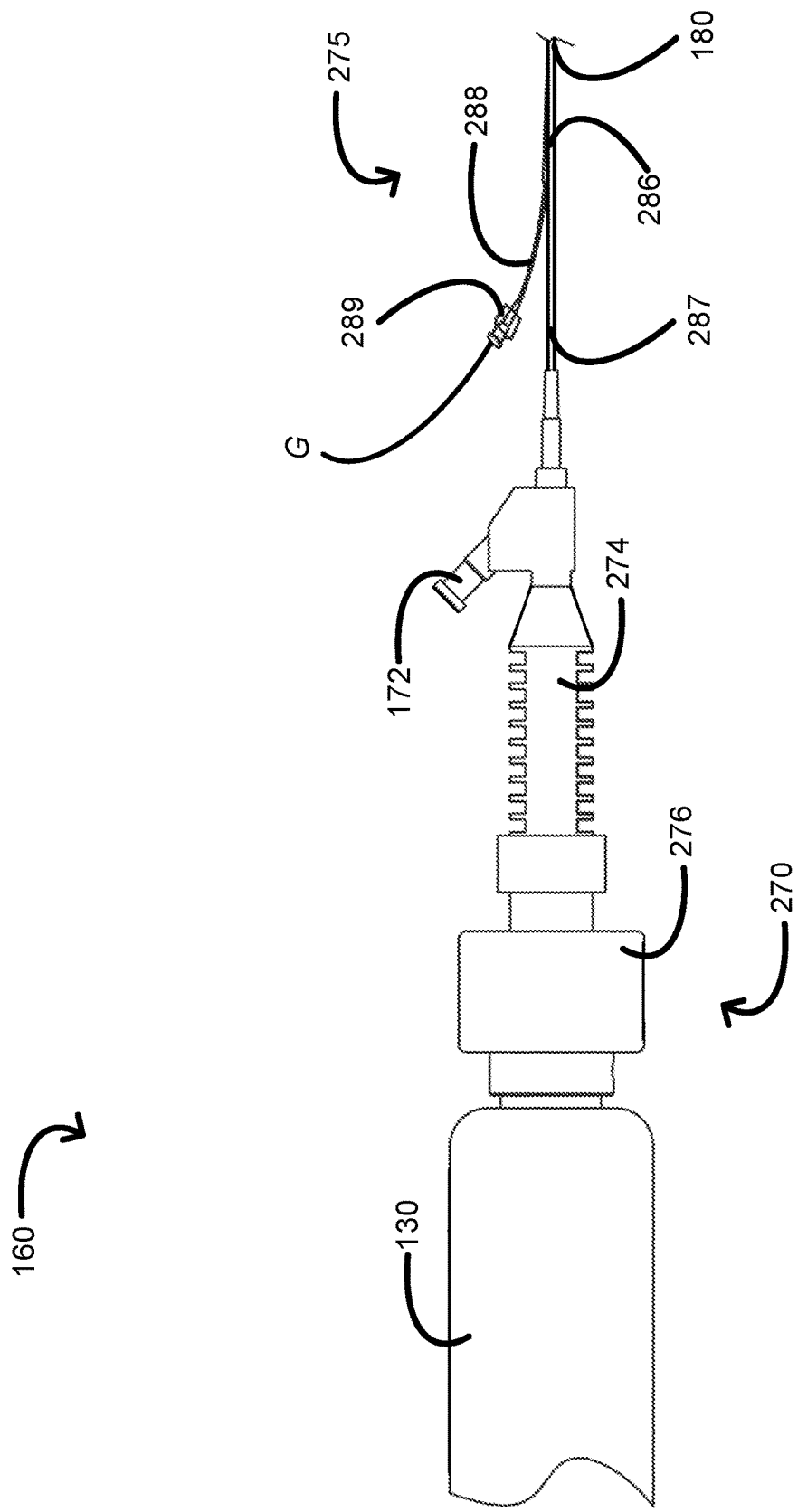

FIG. 2 provides a schematic illustrating a catheter assembly in accordance with some embodiments.

Figure 3:
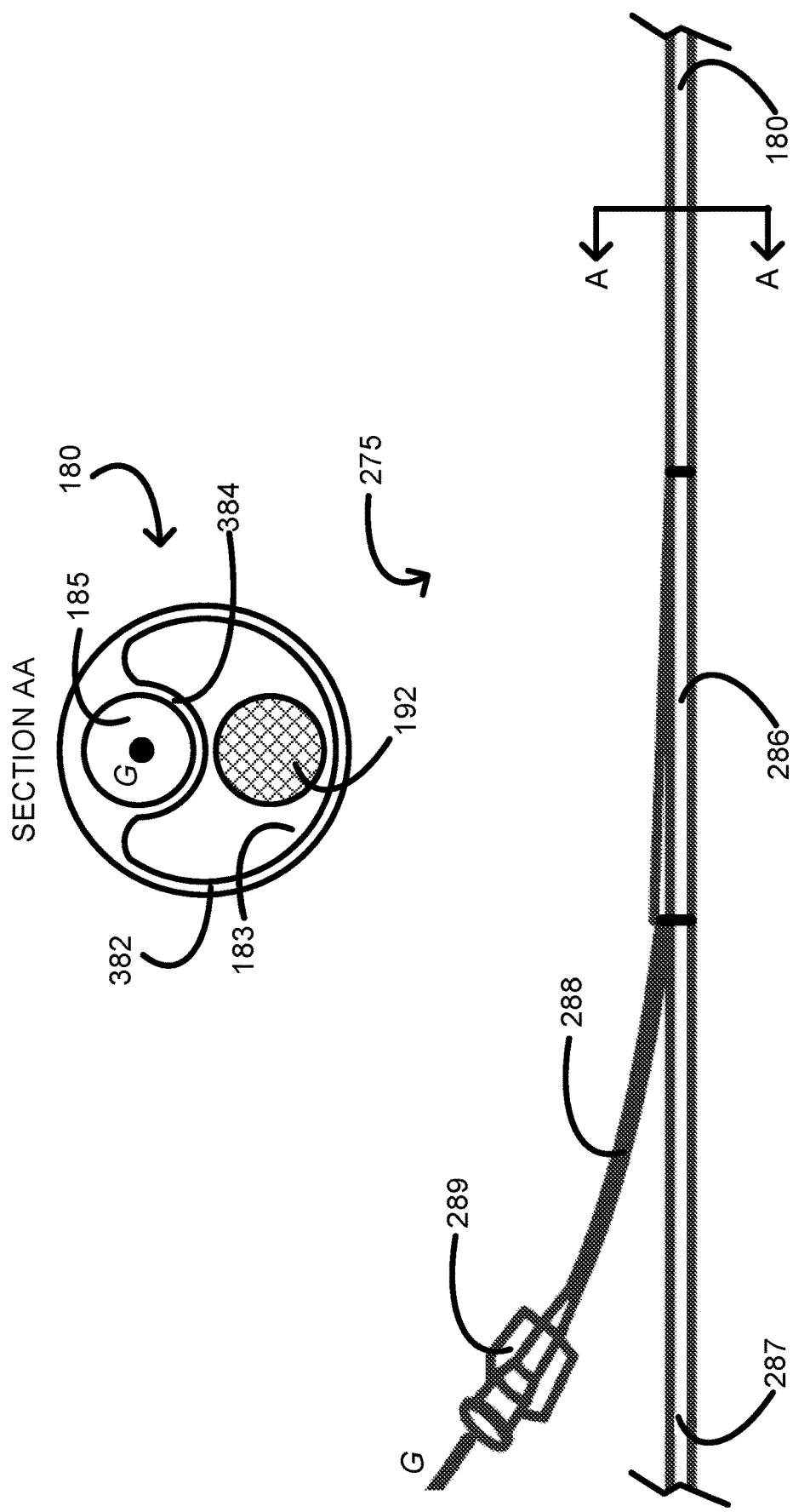

FIG. 3 provides a schematic illustrating a catheter body in accordance with some embodiments.

Figure 4:
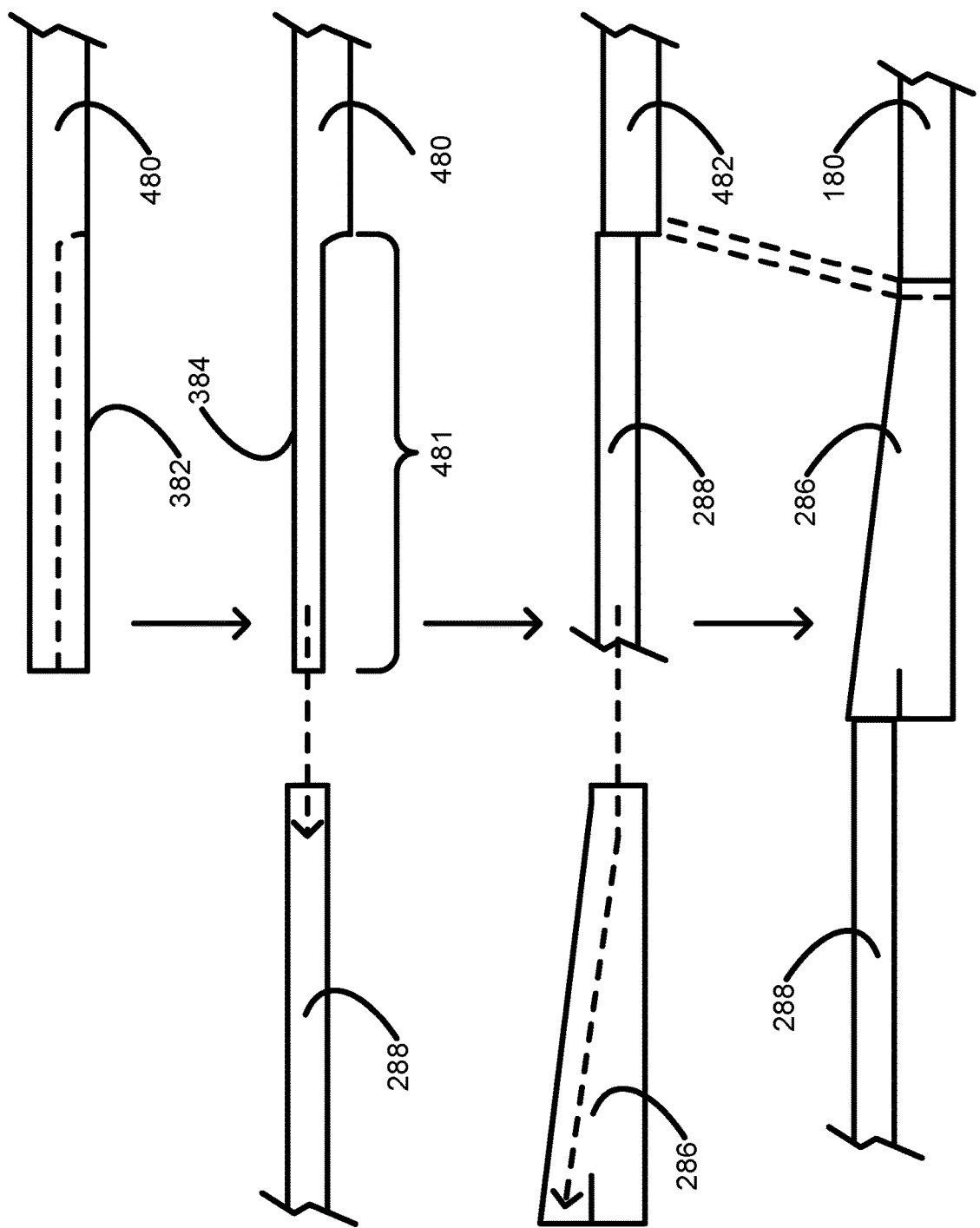

FIG. 4 provides a schematic illustrating a construction of a manifold portion of a catheter assembly in accordance with some embodiments.

Figure 5:
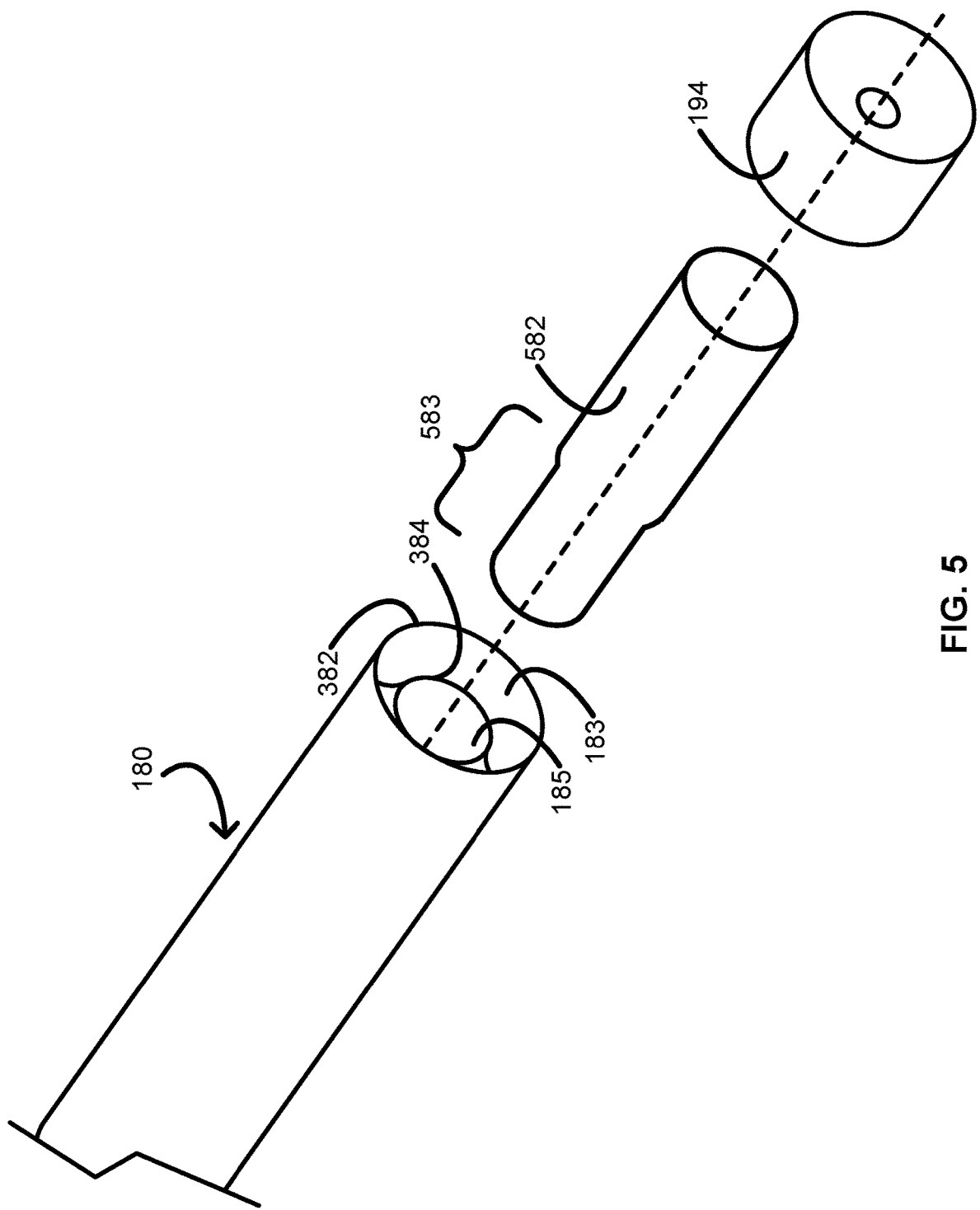

FIG. 5 provides a schematic illustrating a construction of a tip portion of a catheter assembly in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by those of ordinary skill in the art.

An atherosclerotic surgical procedure can involve advancing one or more endoluminal devices to an intravascular lesion to modify the intravascular lesion. For example, angioplasty or atherectomy can involve advancing an over-the-wire ("OTW") endoluminal device over a guidewire in a guidewire lumen of the endoluminal device to an intravascular lesion for modification thereof. However, advancing the OTW endoluminal device to the intravascular lesion can lead to surgical issues from device complications, especially in OTW endoluminal devices having poorly designed or manufactured tube-within-tube designs. For example, a separately extruded, guidewire lumen-containing guidewire tube insufficiently tacked to an inner wall of a sheath of an OTW endoluminal device can lead to device complications such as twisting of portions of the guidewire tube able to move independently from the sheath. Provided herein in some embodiments are dual-lumen catheters, systems, and methods that address the foregoing.

FIG. 1 provides a schematic illustrating a system 100 in accordance with some embodiments. The system 100 includes a console 110 coupled to a catheter assembly 160 configured for modifying intravascular lesions including crossing the intravascular lesions, ablating the intravascular lesions, or a combination of crossing and ablating the intravascular lesions.

As shown in FIG. 1, the system 100 includes the console 110. The console 110 provides a system operator an instrument for monitoring and controlling the system 100 and various sub-systems and functions thereof. The console 110 includes an ultrasonic energy-producing mechanism including an ultrasound generator 120 and an ultrasound transducer 130. Alternatively, the console 110 includes the ultrasound generator 120, the catheter assembly 160 includes the ultrasound transducer 130, and the ultrasonic energy-producing mechanism is divided between the console 110 and the catheter assembly 160. The ultrasonic energy-producing mechanism is configured to convert an electric current into a vibrational energy. For example, the ultrasound generator 120 is configured to convert an alternating electric current (e.g., a current associated with mains electricity) into a high-frequency current (e.g., a current with a frequency commensurate with the operating frequency of the ultrasound transducer 130), and the ultrasound transducer 130, in turn, is configured to convert the high-frequency current into the vibrational energy (e.g., >20 kHz such as 20.5 kHz±500 Hz).

The console 110 optionally further includes a foot switch 140 configured to activate and deactivate the system 100 such as activate and deactivate a core wire 192 (e.g., a nitinol core wire) of the catheter assembly 160. The core wire 192 is disposed in a core-wire lumen 183 of a sheath 180 of the catheter assembly 160. A proximal end of the core wire 192 is vibrationally coupled to the ultrasound transducer 130, and a distal end of the core wire 192 is vibrationally coupled to a lesion-modifying tip member 194. As such, the core wire 192 is configured to transfer the vibrational energy from the ultrasound transducer 130 to the tip member 194 for modifying intravascular lesions. When the system 100 is powered on but not activated, the foot switch 140 is used to activate the system 100, thereby activating the ultrasound transducer 130, the core wire 192, and the tip member 194 of the catheter assembly 160. When the system 100 is powered on and activated, the foot switch 140 is used to deactivate the system 100, thereby deactivating the ultrasound transducer 130, the core wire 192, and the tip member 194 of the catheter assembly 160.

The console 110 optionally further includes an injector 150 configured to inject an irrigant into an irrigation port 172 of the catheter assembly 160. The irrigant is, for example, a sterile liquid (e.g., water, saline, heparinized saline, etc.) for irrigating an anatomical area undergoing an intravascular lesion-modification procedure (e.g., crossing an intravascular lesion, ablating an intravascular lesion, etc.), cooling the core wire 192 of the catheter assembly 160, flushing a guidewire lumen 185 of the sheath 180, or a combination thereof.

The console 110 optionally further includes both the foot switch 140 and the injector 150. In such embodiments, the foot switch 140 is further configured to activate and deactivate the injector 150 when the system 100 is respectively activated and deactivated with the foot switch 140.

FIG. 2 provides a schematic illustrating the catheter assembly 160 in accordance with some embodiments. The catheter assembly 160 includes a housing 270 coupled to a catheter body 275 configured for modifying intravascular lesions including crossing the intravascular lesions, ablating the intravascular lesions, or a combination of crossing and ablating the intravascular lesions.

As shown in FIG. 2, the housing 270 includes the irrigation port 172, a hub 274, and a lock collar 276 for locking the housing 270 onto the ultrasound transducer 130. Locking the housing 270 onto the ultrasound transducer 130 ensures the proximal end of the core wire 192 is sufficiently vibrationally coupled to the ultrasound transducer 130 for modifying intravascular lesions. Again, the catheter assembly 160 alternatively includes the ultrasound transducer 130, which divides the ultrasonic energy-producing mechanism between the console 110 and the catheter assembly 160. In such embodiments, the housing 270 further includes the ultrasound transducer 130 disposed therein at the proximal end of the core wire, thereby obviating the lock collar 276 shown in FIG. 2.

FIG. 3 provides a schematic illustrating the catheter body 275 in accordance with some embodiments. The catheter body 275 includes the sheath 180, a manifold 286, a coupling tube 287, a support tube 288, a guidewire hub 289, and the core wire 192 configured for modifying intravascular lesions including crossing the intravascular lesions, ablating the intravascular lesions, or a combination of crossing and ablating the intravascular lesions.

As shown in FIG. 3, the sheath 180 is formed of or otherwise include a dual-tube extrusion including a first tube 382 with a first lumen 183 (e.g., the core-wire lumen 183) configured for disposal of the core wire 192 therein and a second tube 384 with a second lumen 185 (e.g., the guidewire lumen 185) configured for accommodating a guidewire G. Because the first tube 382 and the second tube 384 of the dual-tube extrusion respectively include the first lumen 183 and the second lumen 185, the sheath 180 is also referred to herein as being formed of or otherwise including a dual-lumen extrusion. In some contexts, the sheath 180 is described, and in some other contexts, the dual-tube extrusion (e.g., the dual-tube extrusion 480 of FIG. 4) is described; however, it should be understood that the sheath 180 and the dual-tube extrusion share certain features, and, thus, description for the sheath 180 applies to the dual-tube extrusion and description for the dual-tube extrusion applies to the sheath 180—unless context clearly dictates otherwise.

The second tube 384 of the dual-tube extrusion is disposed within the first tube 382 of the dual-tube extrusion. In other words, the second lumen 185 of the dual-lumen extrusion is disposed within the first lumen 183 of the dual-lumen extrusion. Furthermore, the second tube 384 of the dual-tube extrusion shares at least a portion of a tube wall with the first tube 382 when the second tube 384 is disposed within the first tube 382 of the dual-tube extrusion. With a shared tube wall, the first tube 382 and the second tube 384 are fixed together along a substantial length thereof, obviating a need for the second tube 384 to be tacked to the first tube 382. As provided herein, insufficiently tacking a separately extruded guidewire tube to an inner wall of a sheath of an endoluminal device can lead to device complications such as twisting of portions of the guidewire tube able to move independently from the sheath.

It should be understood that the dual-tube extrusion is a single extrusion including both the first tube 382 and the second tube 384. Because the dual-tube extrusion already includes the second tube 384 fixed to the first tube 382, a subsequent step of attaching, tacking, bonding, or the like need not be performed to fix the second tube 384 to the first tube 382, which subsequent step, as provided herein, can lead to device complications such as twisting of portions of the guidewire tube able to move independently from the sheath.

The manifold 286 is configured to bifurcate the lumens of the sheath 180 such that the core-wire lumen 183 extends into the coupling tube 287 and the guidewire lumen 185 extends into the support tube 288 opening at the guidewire hub 289 coupled thereto. Such a configuration provides an OTW-type catheter for the catheter assembly 160. Notwithstanding the foregoing, modifications to the catheter assembly 160 can be made to provide rapid-exchange ("RX") or short rapid-exchange ("SRX") catheter assemblies; however, in such embodiments, the dual-tube extrusion portion of the sheath 180 might be shorter in length than that described herein.

The coupling tube 287 is configured to couple the catheter body 275 to the housing 270. The coupling tube 287 includes an extension of the core-wire lumen 183 of the sheath 180. As such, the core wire 192 of the catheter assembly 160 extends from the vibrationally coupled tip member 194 at a distal end of the sheath 180 to the manifold 286 at a proximal end of the sheath 180, through the manifold 286 and at least a portion of the coupling tube 287 disposed therein, through a remaining portion of the coupling tube 287, through the housing 270, and to the vibrationally coupled ultrasound transducer 130.

FIG. 4 provides a schematic illustrating a construction of a manifold portion of the catheter assembly 160 in accordance with some embodiments.

Again, the manifold 286 is configured to bifurcate the lumens of the sheath 180 such that the core-wire lumen 183 extends into the coupling tube 287 and the guidewire lumen 185 extends into the support tube 288. As shown in FIG. 4, a skived proximal-end portion 481 of the sheath 180 including the second tube 384 without the first tube 382 is disposed in the support tube 288, which support tube 288 is, in turn, disposed in the manifold 286, thereby extending the guidewire lumen 185 into the support tube 288 for access through the guidewire hub 289. In other words, the manifold 286 is disposed around the support tube 288, which support tube 288 is, in turn, disposed around at least the skived proximal-end portion 481 of the sheath 180, thereby extending the guidewire lumen 185 into the support tube 288 for access through the guidewire hub 289. In addition, the manifold 286 abuts or be disposed around an adjoining portion of the sheath 180 including the first tube 384 and the second tube 382.

As described herein, the skived portion 481 of the sheath 180 results from skiving off a portion of the first tube 382 enclosing the first lumen 183 in a proximal-end portion of a dual-tube extrusion 480 and leaving the second tube 384 in the skived portion 481. The skived portion 481 of the sheath 180 is less than or equal to about 50 mm long, including less than or equal to about 35 mm long, such as less than or equal to about 25 mm long. For example, the skived portion of the sheath 180 is less than or equal to about 31 mm long.

FIG. 5 provides a schematic illustrating a construction of a tip portion of the catheter assembly 160 in accordance with some embodiments.

As shown in FIG. 5, the tip portion of the catheter assembly 160 includes the tip member 194 (e.g., metal tip member 194) seated in the distal end of the sheath 180. The second lumen 185 (e.g., the guidewire lumen 185) of the sheath 180 extends through the tip member 194 enabling a guidewire to pass through the tip member 194. The distal end of the sheath 180, particularly a distal end of the second tube 384, includes a flared portion. The flared portion of the second tube 384 is flared to about 2-6 mm, including about 3-5 mm, for example, about 4 mm. A sized-matched or necked-down portion 583 of a piece of guidewire tubing 582 is disposed in the flared portion of the second tube 384 enabling the tip member 194 to be seated in the distal end of the sheath 180, thereby extending the second lumen 185 of the sheath 180 through the tip member 194 for a guidewire.

While not expressly shown in FIG. 5, a distal end portion of the sheath 180 including the distal end thereof is tapered. It should be understood that in embodiments of the catheter assembly 160 not including such a taper, the second tube 384 need not be flared or need not be flared as much to accommodate the piece of guidewire tubing 582. Furthermore, the piece of guidewire tubing 582 need not be necked down or necked down as much in such embodiments.

The piece of guidewire tubing 582 is formed of a biocompatible material, including a biocompatible polymer, such as polyether block amide, for example, Pebax®. The support tube 288 (see FIG. 4) is formed of a same or different material, polymer, or polyether block amide.

Referring to FIGS. 4 and 5, a method for manufacturing the catheter assembly 160 includes construction of the manifold portion and the tip portion of the catheter assembly 160. Constructing the manifold portion of the catheter assembly 160 includes extruding the dual-tube extrusion 480, skiving off a portion of the dual-tube extrusion 480, and disposing the dual-tube extrusion 480 in the manifold 286. Constructing the tip portion of the catheter assembly 160 includes flaring a portion of the dual-tube extrusion 480, and seating the tip member 194 in the dual-tube extrusion 480. In some embodiments, the method further includes disposing the core wire 192 in the first lumen 183 of the dual-tube extrusion 480.

With respect to constructing the manifold portion, extruding the dual-tube extrusion 480 includes extruding a biocompatible material to form the dual-tube extrusion 480 including the first tube 382 with the first lumen 183 and the second tube 384 with the second lumen 185. The second tube 384 is disposed within the first tube 382 in the dual-tube extrusion 480, and the second tube 384 and the first tube 382 share a wall in the dual-tube extrusion 480. The first lumen 183 is configured for disposing the core wire 192 therein, and the second lumen 185 is configured to accommodate a guidewire. Skiving off the portion of the dual-tube extrusion 480 includes skiving off the first tube 382 in the proximal-end portion of the dual-tube extrusion 480 to provide the skived portion 481 of the dual-tube extrusion 480, which includes the second tube 384 without the first tube 382. Disposing the dual-tube extrusion 480 in the manifold 286 includes disposing the second tube 384 of the skived portion 481 of the dual-tube extrusion 480 in the support tube 288. Subsequently, the support tube 288 including the second tube 384 of the skived portion 481 is disposed in the manifold 286 optionally with an adjoining portion of the dual-tube extrusion 480 including the first tube 382 and the second tube 384. The method further includes attaching the guidewire hub 289 to the support tube 288.

Extruding the dual-tube extrusion 480 to form the second tube 384 within the first tube 382 with the shared tube wall obviates a need for the second tube 384 to be tacked to the first tube 382. As provided herein, insufficiently tacking a separately extruded guidewire tube to an inner wall of a sheath of an endoluminal device can lead to device complications such as twisting of portions of the guidewire tube able to move independently from the sheath. Furthermore, tacking the separately extruded guidewire tube to the inner wall of the sheath requires more steps and, thus, more time than extruding the dual-tube extrusion 480 described herein.

With respect to constructing the tip portion, flaring the portion of the dual-tube extrusion 480 includes flaring the second tube 384 in the distal-end portion of the dual-tube extrusion 480 to provide a flared portion of the second tube 384. Seating the tip member 194 in the dual-tube extrusion 480 includes disposing the size-matched piece of guidewire tubing 582 in the flared portion of the second tube 384. Subsequently, a metal, lesion-modifying tip member 194 is seated in the distal end of the dual-tube extrusion 480.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A catheter assembly configured for modifying intravascular lesions, comprising:
   a core wire including a proximal end configured to vibrationally couple to an ultrasound transducer;
   a dual-lumen extrusion including a first lumen and a second lumen, wherein:
      the core wire is disposed within the first lumen, and
      the second lumen is configured to accommodate a guidewire;
   a manifold disposed around at least a skived proximal-end portion of the dual-lumen extrusion, wherein the skived proximal-end portion includes the second lumen without the first lumen, and
   a tip member seated in a distal end of the dual-lumen extrusion,
      wherein the second lumen of the dual-lumen extrusion extends through the tip member enabling the guidewire to pass through the tip member, and
      wherein the distal end of the dual-lumen extrusion includes a flared portion of the dual-lumen extrusion, and a sized-matched piece of guidewire tubing is disposed in the flared portion extending the second lumen of the dual-lumen extrusion through the tip member.

2. The catheter assembly of claim 1, wherein the second lumen is disposed within the first lumen in the dual-lumen extrusion.

3. The catheter assembly of claim 1, wherein the skived proximal-end portion of the dual-lumen extrusion is less than or equal to about 35 mm long.

4. The catheter assembly of claim 1, wherein:
   the skived proximal-end portion of the dual-lumen extrusion is disposed in a support tube, and
   the manifold is disposed around the support tube and an adjoining portion of the dual-lumen extrusion including the first lumen and the second lumen.

5. The catheter assembly of claim 1, further comprising an ultrasound transducer at the proximal end of the core wire.

6. A system configured for modifying intravascular lesions, comprising:
   a) a catheter assembly, including:
      a core wire;
      a dual-tube extrusion including a first tube with a first lumen and a second tube with a second lumen, wherein:
         the core wire is disposed within the first lumen, and
         the second lumen is configured to accommodate a guidewire; and
      a manifold disposed around at least a skived proximal-end portion of the dual-tube extrusion, wherein the skived proximal-end portion includes the second tube without the first tube; and a tip member seated in a distal end of the dual-tube extrusion,
wherein the second lumen of the dual-tube extrusion extends through the tip member enabling the guidewire to pass through the tip member, and
wherein the distal end of the dual-tube extrusion includes a flared portion of the second tube, and a size-matched piece of guidewire tubing is disposed in the flared portion of the second tube extending the second lumen of the dual-tube extrusion through the tip member; and
b) an ultrasonic energy-producing mechanism, including:
an ultrasound generator; and
an ultrasound transducer, wherein a proximal end of the core wire is configured to vibrationally couple to the ultrasound transducer.

7. The system of claim 6, wherein:
the second tube is disposed within the first tube of the dual-tube extrusion, and
the second tube shares at least a portion of a tube wall with the first tube.

8. The system of claim 6, wherein:
the second tube of the skived proximal-end portion of the dual-tube extrusion is disposed in a support tube, and
the manifold is disposed around the support tube and an adjoining portion of the dual-tube extrusion including the first tube and the second tube.

9. The system of claim 6, further comprising:
c) a console including a foot switch and the ultrasonic energy-producing mechanism including the ultrasound generator and the ultrasound transducer, wherein the foot switch is configured to activate and deactivate the ultrasonic energy-producing mechanism.

10. The system of claim 6, further comprising:
c) a console including a foot switch and the ultrasound generator of the ultrasonic energy-producing mechanism, wherein:
the catheter assembly further includes the ultrasound transducer of the ultrasonic energy-producing mechanism, and
the foot switch is configured to activate and deactivate the ultrasonic energy-producing mechanism.

* * * * *